United States Patent [19]

Tobiki et al.

[11] 4,008,220
[45] Feb. 15, 1977

[54] PENICILLINS

[75] Inventors: Hisao Tobiki, Osaka; Hirotada Yamada, Hyogo; Iwao Nakatsuka, Osaka; Kozo Shimago, Hyogo; Shigeru Okano, Hyogo; Takenari Nakagome, Hyogo; Toshiaki Komatsu, Hyogo; Akio Izawa, Osaka; Hiroshi Noguchi, Hyogo; Yasuko Eda, Osaka, all of Japan

[73] Assignee: Sumitomo Chemical Company, Limited, Japan

[22] Filed: Aug. 8, 1974

[21] Appl. No.: 495,914

Related U.S. Application Data

[63] Continuation-in-part of Ser. No. 341,723, March 15, 1973, abandoned.

[30] Foreign Application Priority Data

Mar. 15, 1972 Japan .................. 47-26759

[52] U.S. Cl. .................. 260/239.1; 424/271
[51] Int. Cl.² .................. C07D 499/48
[58] Field of Search .................. 260/239.1

[56] References Cited
UNITED STATES PATENTS 3,770,722  11/1973  Bright et al. .................. 260/239.1
3,873,523  3/1975  Doub et al. .................. 260/243 C

*Primary Examiner*—Donald G. Daus
*Assistant Examiner*—Mary C. Vaughn
*Attorney, Agent, or Firm*—Stewart and Kolasch, Ltd.

[57] ABSTRACT

A penicillin of the formula:

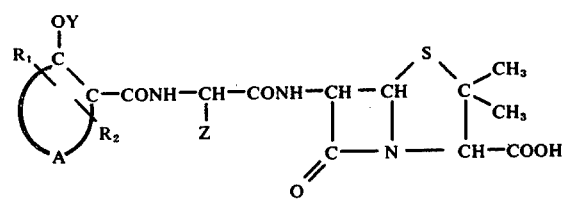

wherein

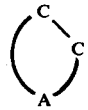

is a six-membered heteroaromatic ring containing 1 or 2 nitrogen atoms as the hetero atom, Y is hydrogen, lower alkanoyl or lower alkoxycarbonyl, $R_1$ and $R_2$ are each hydrogen, lower alkyl, lower alkanoyl, benzoyl, lower alkylmercapto, hydroxyl, mercapto, hydroxy(-lower)alkyl, halogen or cyano or $R_1$ and $R_2$ may link together to form a lower alkylene chain which may be substituted with an oxo group, and Z is phenyl, hydroxyphenyl, lower alkyl, cyclohexadienyl, thienyl or isothiazolyl, which is prepared by reacting a compound of the formula:

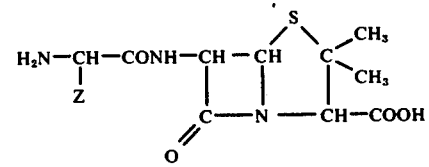

wherein Z is as defined above or its derivative with a carboxylic acid of the formula:

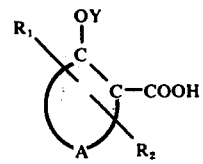

wherein

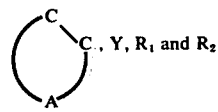

, Y, $R_1$ and $R_2$ and $R_2$ are each as defined above or its reactive derivative, if necessary, followed by hydrolysis or acylation of the resulting product and/or elimination of any protective group and which is useful as an antimicrobial agent against various gram-positive and gram-negative bacteria including Pseudomonas.

20 Claims, No Drawings

PENICILLINS

This is a continuation-in-part application of Application Ser. No. 341,723, filed Mar. 15, 1973, now abandoned.

This invention relates to penicillins and their production. More particularly, it relates to novel 6-(aminoacylamido)-penicillanic acid derivatives and their non-toxic, pharmaceutically acceptable salts, and to their production.

As is well known, 6-(α-aminophenylacetamido)-penicillanic acid (i.e. ampicillin) inhibits the growth of various gram-positive and gram-negative bacteria but does not exert any appreciable antimicrobial activity against Pseudomonas. In U.S. Pat. No. 3,433,784, there are described some N-acyl derivatives of said ampicillin as showing a minimal inhibitory concentration of 125 to 250 μg/ml against *Pseudomonas pyocinea* A or R 59, when determined by the standard test method. The anti-Pseudomonas activity of the compounds as described in the working examples is, however, not so high and the antimicrobial activity against other gram-positive and gram-negative bacteria is considerably low. Thus, it may be said that the N-acyl derivatives of ampicillin are less valuable from the practical viewpoint.

As the result of the study seeking novel penicillins which have a broad antimicrobial spectrum and are highly active against gram-positive and gram-negative bacteria including Pseudomonas, it has been found that, among various compounds, the penicillins of the following formula characteristically exhibit a noticeable antimicrobial activity against Pseudomonas and a broad antimicrobial spectrum:

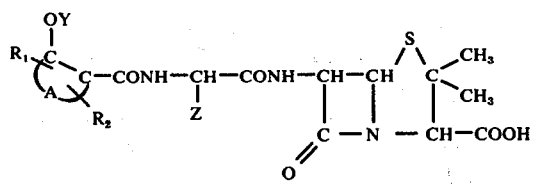

(I)

wherein

is a six-membered heteroaromatic ring containing 1 to 2 nitrogen atoms as the hetero atom, Y is hydrogen, lower alkanoyl or lower alkoxycarbonyl, $R_1$ and $R_2$ are each hydrogen, lower alkyl, lower alkanoyl, benzoyl, lower alkylmercapto, hydroxyl, mercapto, hydroxy(lower)alkyl, halogen or cyano or $R_1$ and $R_2$ may link together to form a lower alkylene chain which may be substituted with an oxo group, and Z is phenyl, hydroxyphenyl, lower alkyl cyclohexadienyl, thienyl or isothiazolyl.

The term "lower alkyl" as used hereinabove is intended to mean both straight and branched chain aliphatic hydrocarbons having from one to eight carbon atoms such as methyl, ethyl, propyl, isopropyl, butyl, isobutyl, amyl and isoamyl. Similarly where the term lower is used as a part of the description of any other group (e.g. lower alkoxy, lower alkanoyl, lower alkylmercapto), it refers to the alkyl portion of such group. The heteroaromatic ring may be, for example, pyridine, pyrimidine, pyridazine or pyrazine.

The pharmaceutical characteristics of the penicillins of the formula (I) are their strong antimicrobial activity against Pseudomonas, broad antimicrobial spectrum, low toxicity and high solubility in water, which is desirable in the injectable formulations.

The structural characteristics of the new penicillins of the formula (I) are that the residue

bears thereon one or more —O—Y groups and that one of these groups is linked to a carbon atom adjacent to the carbon atom to which an N-acylpenicillin unit is linked. The compounds wherein the residue

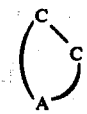

bears no —O—Y group are antimicrobially much less active than those bearing an —O—Y group and exhibit only the same low antimicrobial activity as those disclosed in U.S. Pat. No. 3,433,784 against Pseudomonas as well as other gram-positive and gram-negative bacteria.

In case of Z being phenyl and

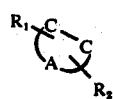

representing a pyridine ring, the preferred penicillins (I) are those wherein $R_1$ and $R_2$ are each hydrogen, lower alkyl (particularly methyl), cyano, hydroxy (lower)alkyl (particularly α-hydroxyethyl), lower alkanoyl (particularly acetyl) or benzoyl or they are linked together so that represents a $C_8$—$C_{10}$ cycloalkenopyridine ring (e.g. cyclopentenopyridine, cyclohexenopyridine, cycloheptenopyridine) which may be substituted with an oxo group and Y is hydrogen, ethoxycarbonyl or t-butanoyl. In case of Z being phenyl and

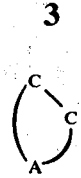

representing a pyrimidine ring, the preferred penicillins (I) are those wherein $R_1$ and $R_2$ are each hydrogen, hydroxyl, mercapto or lower alkylthio (particularly methylthio) and Y is hydrogen or ethoxycarbonyl. In case of Z being phenyl and

representing a pyridazine ring, the preferred penicillins (I) are those wherein $R_1$ and $R_2$ are each hydrogen, halogen (particularly chlorine) or lower alkyl (particularly methyl) and Y is hydrogen.

Among the penicillins (I), particularly effective are D-α-(4-hydroxypyridine-3-carboxamido)-benzylpenicillin, D-α-(2,4-dihydroxypyrimidine-5-carboxamido)-benzylpenicillin, D-α-(3-hydroxypyridazine-4-carboxamido)-benzylpenicillin, D-α-(3-hydroxypyridine-2-carboxamido)-benzylpenicillin, D-α-(2-hydroxypyridine-3-carboxamido)-benzylpenicillin, D-α-(2-hydroxypyrazine-3-carboxamido)-benzylpenicillin, D-α-(4-hydroxypyridine-3-carboxamido)-p-hydroxybenzylpenicillin, D-α-(2-hydroxypyridine-3-carboxamido)-p-hydroxybenzylpenicillin, etc.

According to the present invention, the penicillin (I) can be produced by reacting the compound of the formula:

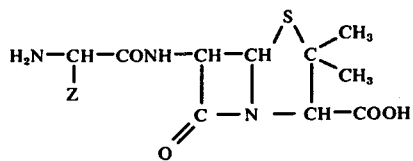

wherein Z is an defined above or its derivative with a carboxylic acid of the formula:

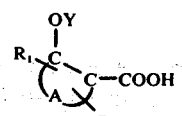

wherein

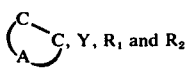

Y, $R_1$ and $R_2$ and $R_2$ are each as defined above or its reactive derivative, if necessary, followed by hydrolysis or acylation of the resulting product and/or elimination of any protective group.

The derivative of the compound (II) may be, for example, salts, esters and N-substituted compounds thereof. Examples of the salts are salts of alkali metals (e.g. sodium, potassium), alkaline earth metals (e.g. calcium, barium), organic bases (e.g. trimethylamine, triethylamine) and organic sulfonic acids (e.g. toluenesulfonic acid, naphthalenesulfonic acid, tetrahydronaphthalenesulfonic acid). Examples of the esters and the N-substituted compounds are as follows:

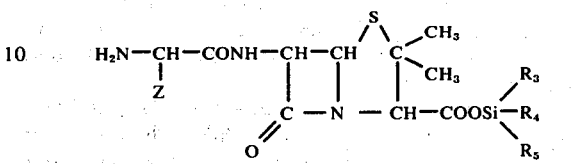

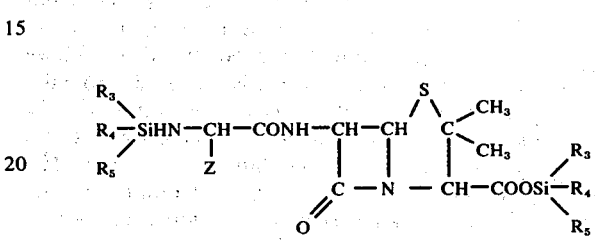

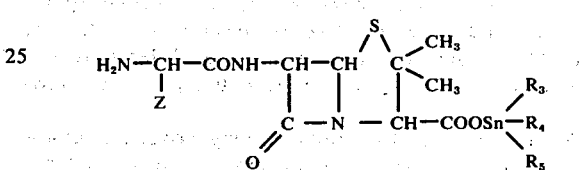

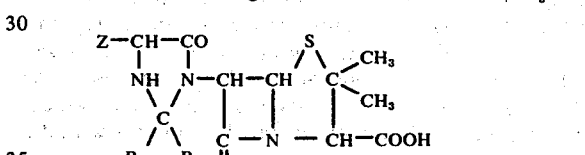

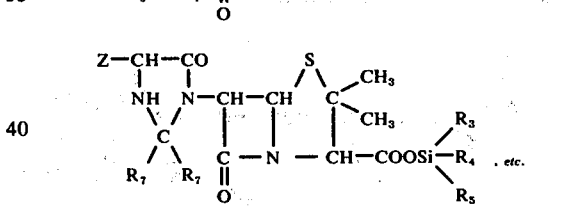

wherein $R_3$, $R_4$, $R_6$ and $R_7$ are each a lower alkyl group and Z is as defined above.

Further examples of the ester unit constructing the esters of the compound (II) are as follows: toluenesulfonylethylester, p-nitrobenzylester, benzylester, phenacylester, diphenylmethylester, substituted diphenylmethylester, tritylester, benzoyloxymethylester, lower alkanoyloxymethylester, dimethylmethyleneaminoester, p-nitrophenylester, methylsulfonylphenylester, methylthiophenylester, t-butylester, 3,5-di-t-butyl-4-hydroxybenzylester and trichloroethylester. These ester units are all conventionally employed as a group protecting a carboxylic acid radical in the field of Penicillin, Cephalosporin or Peptide Chemistry. Furthermore, the salts of the esters as above mentioned of the compound (II), for example, salts of hydrochloric acid and organic sulfonic acids (e.g. toluenesulfonic acid, naphthalenesulfonic acid, tetrahydronaphthalenesulfonic acid) can also be employed. In this case esters derived from penicillin G by the well-known method are preferable.

The compound (III) may be used as such, i.e. in a free or salt form, or as the reactive derivative.

Examples of salts of the compound (III) are the salts of alkali metals, alkaline earth metals, ammonia and organic bases (e.g. trimethylamine, triethylamine, dicyclohexylamine).

The reactive derivatives of the compound (III) on the carboxyl group include, e.g. acid halides, acid anhydrides, active amides, acid azides and active esters.

Among the acid halides, the use of an acid chloride is the most favorable. Examples of the acid anhydrides are mixed acid anhydrides and symmetric acid anhydrides prepared by the use of acids such as toluenesulfonic acid, an alkylcarbonic acid and an aliphatic carboxylic acid (e.g. pivalic acid). Examples of the active amides are those obtained by using imidazole, dimethylpyrazole, triazole, tetrazole or the like. Examples of the active esters are those prepared by using p-nitrophenol, pentachlorophenol, p-nitrothiophenol, N,N'-di-methylhydroxylamine, 1-hydroxy-2(1H)-pyridone, N-hydroxy-succinimide or N-hydroxyphthalimide.

When the compound (III) wherein Y is hydrogen or its reactive derivative is used, the hydroxyl group may be protected with any protecting group as is conventionally employed in the related art field.

Illustrating some of the reactive derivatives of the compound (III) in detail, the mixed acid anhydride of the formula:

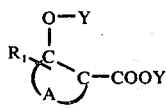

(IV)

where

$R_1$ and $R_2$ are each as defined above, and Y represents acyl or alkoxycarbonyl can be prepared by the reaction of the compound (III) wherein Y is hydrogen with an acyl halide or an alkyl halocarbonate. Thus, the reaction of 1 molar amount of the compound (III) with 2 molar amount of an acyl halide (e.g. pivaloyl chloride) or an alkyl halocarbonate (e.g. ethyl chlorocarbonate, isobutyl chlorocarbonate) in the presence of 2 molar amount of a basic substance may afford the compound (IV) in an excellent yield. (the process using the thus obtained mixed acid anhydride (IV) as the reactant will be referred to as the "mixed anhydride process".)

Another type of the reactive derivative is the compound of the formula:

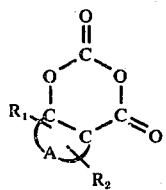

(V)

wherein

$R_1$ and $R_2$ are each as defined above, which may be prepared by the reaction of 1 molar amount of the compound (III) with 1 molar amount of phosgene in the presence of 2 molar amount of a basic substance. The similar type of the reactive derivative may be also prepared by the use of thionyl chloride, phosphorus trichloride or the like in place of phosgene. (The process using the above cyclic compound (V) or any similar compound thereto as the reactant will be referred to as the "phosgene process".)

Examples of the basic substance in the said reactions are an inorganic base (e.g. sodium hydroxide, potassium hydroxide) and an organic base (e.g. triethylamine, pyridine, dimethylaniline, lutidine, N-methylmorpholine and N-methylpiperidine).

As the reactive derivatives above prepared are usually so reactive and unstable to be isolated they are used in the form of the reaction mixture for the reaction with the compound (II).

Among the compound (III), there is included a pyridine carboxylic acid of the formula:

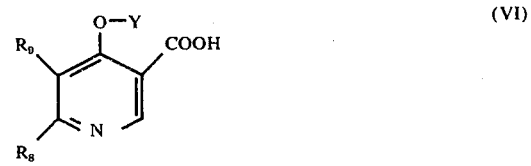

wherein Y is as defined above, $R_8$ is hydrogen or lower alkyl and $R_9$ is lower alkyl, lower alkanoyl, cyano, hydroxy(lower)-alkyl or benzoyl or $R_8$ and $R_9$ are linked together to form lower alkylene, which may be prepared by condensing a ketone of the formula:

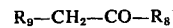

wherein $R_8$ and $R_9$ are each as defined above with diethyl aminomethylenemalonate of the formula:

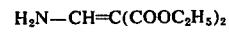

and cyclizing the resultant condensation product, followed by hydrolysis. The said compound (VI) may be also produced by condensing an unsaturated amine of the formula:

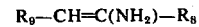

wherein $R_8$ and $R_9$ are each as defined above with diethyl ethoxymethylenemalonate of the formula:

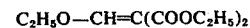

and cyclizing the resultant condensation product, followed by hydrolysis.

The compound (VI) wherein $R_9$ is lower alkanoyl may be reduced to give the compound (VI) wherein $R_9$ is hydroxy(lower)alkyl. Further, the compound (VI) wherein Y is hydrogen may be acylated by a conventional procedure to give the compound (VI) wherein Y is lower alkanoyl or lower alkoxycarbonyl.

Specific examples of the compound (III) are as follows:

4-Hydroxy-2,3-cyclopentenopyridine-5-carboxylic acid, m.p. 263°–264° C (decomp.);
4-Hydroxy-2,3-cyclohexenopyridine-5-carboxylic acid, m.p. 285° C (decomp.);

4-Hydroxy-2,3-cycloheptenopyridine-5-carboxylic acid, m.p. 248°–249° C (decomp.);
2-Methyl-3-acetyl-4-hydroxypyridine-5-carboxylic acid, m.p. 260°–263° C (decomp.);
4-Hydroxy-2-methyl-3-benzoylpyridine-5-carboxylic acid, m.p. >360° C;
2-Methyl-3-(α-hydroxyethyl)-4-hydroxypyridine-5-carboxylic acid, m.p. >360° C;
4-Hydroxy-6,7-dihydro-5-oxo-5H-cyclopenta[b]pyridine-3-carboxylic acid, m.p. >300° C;
2-Methyl-3-cyano-6-hydroxypyridine-5-carboxylic acid, m.p. 247°–248° C, etc.

The reaction between the compound (II) or its derivative and the compound (III) or its reactive derivative is usually carried out in an inert solvent such as a polar solvent (e.g. dichloromethane, chloroform, acetone, tetrahydrofuran, dioxane, acetonitrile, methylisobutylketone, ethyl alcohol, dimethylformamide), a nonpolar solvent (e.g. benzene, toluene, petroleum ether, n-hexane) or their mixture. In some cases, there may be used an aqueous medium. The reaction temperature is not limitative and is usually below 50° C, preferably from 50° to −80° C.

When the compound (III) is employed in the form of a free acid or a salt, there is preferably used a coupling reagent such as N,N'-dicyclohexylcarbodiimide, N-cyclohexyl-N'-morpholinoethylcarbodiimide, triphenylphosphine or 2-ethyl-5-(m-sulfonyl)-isoxazolium hydroxide inner salt in the reaction with the compound (II). In case of using such coupling reagent, the reaction often proceeds through the activated state of the carboxyl group in the compound (III), or the activated state of the amino group in the compound (II).

When the compound (I) wherein Y is lower alkanoyl or lower alkoxycarbonyl is produced, it may be further hydrolyzed in the presence of an inorganic base (e.g. sodium carbonate, potassium carbonate, sodium hydroxide, ammonia), an organic base (e.g. methylamine, dimethylamine, diethylamine, triethylamine, benzylamine, morpholine, piperidine, potassium 2-ethylhexanoate, sodium 2-ethylhexanoate), an inorganic acid (e.g. hydrochloric acid, sulfuric acid) or an organic acid (e.g. formic acid, trifluoroacetic acid, methanesulfonic acid) to give the corresponding compound (I) wherein Y is hydrogen.

When any protective group is present in the resulting product, it may be eliminated by a per se conventional procedure such as catalytic reduction or hydrolysis, favorably under a mild condition.

The produced penicillin (I) may be, if desired, converted into its non-toxic pharmaceutically acceptable salt in a per se conventional manner. Examples of the salts are salts of alkali metals (e.g. sodium, potassium), salts of alkaline earth metals (e.g. calcium, magnesium), an ammonium salt, substituted ammonium salts, amine salts (e.g. triethylamine, procaine, dibenzylamine, N-benzyl-β-phenethylamine, 1-ephenamine, N,N'-dibenzylethylenediamine, dehydroabietylamine, N,N'-bis-dehydroabietylethylenediamine salts), an arginine salt, etc.

Practical and presently preferred embodiments of the present invention are illustratively shown in the following Examples.

EXAMPLE 1

Preparation of D-α-(4-ethoxycarbonyloxy-2,3-cyclopentenopyridine-5-carboxamido)-benzylpenicillin:

To 4-hydroxy-2,3-cyclopentenopyridine-5-carboxylic acid (m.p. 263°–264° C, decomp.)(1 g) are added dichloromethane (50 ml) and triethylamine (1.07 g), and the resulting mixture is cooled down to −10° C. Ethyl chlorocarbonate (1.16 g) is added to the mixture which is subsequently stirred at the same temperature for 10 minutes. α-Aminobenzylpenicillin triethylamine salt (2.51 g) is added thereto, and the resulting mixture is kept at −10° to 5° C for 3 hours. On completion of the reaction, a solution of sodium bicarbonate (0.89 g) in water (25 ml) and ethyl acetate (200 ml) are added thereto. The organic layer is separated from the aqueous layer and washed with water (25 ml). The aqueous layer and the washings are combined together, washed twice with 50 ml portions of ethyl acetate, and then cooled with ice. The aqueous solution is adjusted to pH 2 by the addition of dilute aqueous hydrochloric acid and extracted with ethyl acetate (100 ml). The extract is washed with water, dried over anhydrous magnesium sulfate and concentrated under reduced pressure. The residue is recrystallized from ether to give the objective penicillin. Yield, 2.07 g. Purity (determined by iodometry), 93%.

EXAMPLE 2

Preparation of D-α-(4-hydroxy-2,3-cyclopentenopyridine-5-carboxamido)-benzylpenicillin:

To the penicillin (0.9 g) obtained in Example 1 is added a solution of potassium carbonate (0.39 g) in water (9 ml), and the resulting solution is stirred at room temperature for 1 hour and then adjusted to pH 2 with dilute hydrochloric acid while cooling with ice. Separated white crystals are collected by filtration, washed with water and dried under reduced pressure to give the objective penicillin. Yield, 0.6 g. Purity (determined by iodometry), 87%.

EXAMPLE 3

Preparation of D-α-(4-hydroxy-2,3-cyclohexenopyridine-5-carboxamido)-benzylpenicillin:

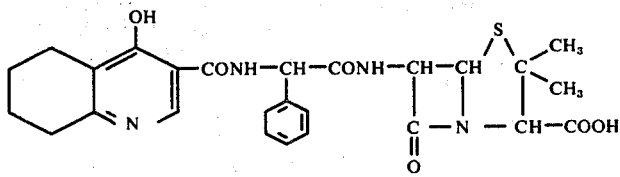

To 4-hydroxy-2,3-cyclohexenopyridine-5-carboxylic acid (hemihydrate, m.p. 285° C, decomp.) (0.9 g) are added dichloromethane (20 ml) and triethylamine (0.9 g), and a 10% solution of phosgene in dichloromethane (4.4 g) is added thereto at −30° C. After stirring for 20 minutes, α-aminobenzylpenicillin triethylamine salt (2 g) is added, and the resulting solution is stirred at the same temperature for 3 hours and then at −5° to 0° C for 1 hour. A solution of potassium carbonate (0.615 g) in water (25 ml) and ethyl acetate (200 ml) are added thereto. The aqueous layer is separated and washed with ethyl acetate. The aqueous solution is adjusted to pH 2 with dilute hydrochloric acid while cooling with ice, and the separated crystals are collected by filtration, washed with water and dried under reduced pressure to give the objective penicillin. Yield, 1.52 g. Purity (determined by iodometry), 90.5%.

EXAMPLE 4

Preparation of D-α-(3-acetyl-4-hydroxy-2-methylpyridine-5-carboxamido)-benzylpenicillin:

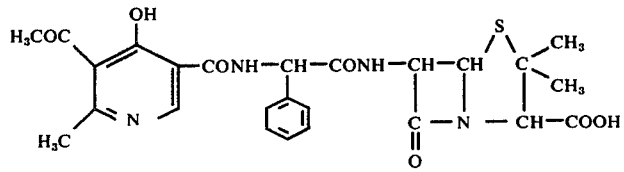

(1) To 3-acetyl-4-hydroxy-2-methylpyridine-5-carboxylic acid (2.38 g) are added dichloromethane (40 ml) and triethylamine (2.5 g), and ethyl chlorocarbonate (2.66 g) is added thereto at −20° C. After 15 minutes, a solution of α-aminobenzylpenicillin triethylamine salt (5.5 g) in dichloromethane (25 ml) is added thereto at the same temperature. After being kept at −10° C for 4 hours, dichloromethane is distilled off under reduced pressure, and the residue is dissolved in a solution of potassium carbonate (1.66 g) in water (100 ml) and ethyl acetate (50 ml). The aqueous layer is separated, allowed to stand at room temperature for 1 to 2 hours, cooled with ice, adjusted to pH 2 with dilute hydrochloric acid and extracted with ethyl acetate. The extract is washed with water, dried over anhydrous magnesium sulfate and distilled under reduced pressure to remove ethyl acetate. The residue is crystallized from petroleum ether to give the objective penicillin. Yield, 5 g. Purity (determined by iodometry), 89%.

2. To 3-acetyl-4-hydroxy-2-methylpyridine-5-carboxylic acid (2.38 g) are added dichloromethane (40 ml) and triethylamine (2.5 g), and ethyl chlorocarbonate (2.66 g) is added thereto at −5° C. After stirring for 30 minutes, the solution is added at 0° to −5° C to a solution of α-aminobenzylpenicillin trimethylsilyl ester in dichloromethane prepared by adding trimethylchlorosilane (1.33 g) to a solution of α-aminobenzylpenicillin triethylamine salt (5.5 g) in dichloromethane (30 ml). The resulting mixture is kept at the same temperature for 5 hours. After removal of dichloromethane under reduced pressure, water (70 ml) is added to the residue, and the resulting mixture is adjusted to pH 2 with concentrated hydrochloric acid while stirring. The precipitate is extracted with ethyl acetate, and the extract is washed with water, dried over anhydrous magnesium sulfate and concentrated under reduced pressure. The residue is dissolved in a solution of potassium carbonate (1.66 g) in water (70 ml) and ethyl acetate (50 ml). The aqueous layer is separated and treated as in the above (1) to give the objective penicillin.

EXAMPLE 5

Preparation of D-α-(2,3-cyclohexeno-4-pivaloyloxypyridine-5-carboxamido)-benzylpenicillin:

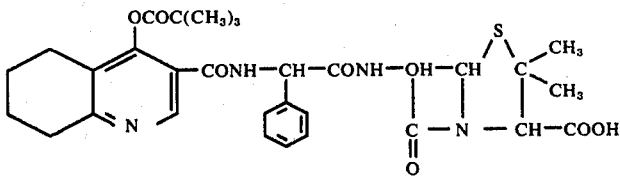

To 4-hydroxy-2,3-cyclohexenopyridine-5-carboxylic acid (0.9 g) are added dichloromethane (30 ml) and triethylamine (0.9 g), and pivaloyl chloride (1.22 g) is added dropwise thereto at −10° C. After stirring for 30 minutes, α-aminobenzylpenicillin sodium salt (1.65 g) is added thereto at the same temperature. The resulting mixture is kept overnight at the same temperature, and cold water (30 ml) and ethyl acetate (200 ml) are added thereto. The aqueous layer is separated at 0° to 5° C, washed with cold ethyl acetate, adjusted to pH 2 with dilute hydrochloric acid and extracted with cold ethyl acetate. The extract is washed with cold water, dried over anhydrous magnesium sulfate and concentrated to dryness under reduced pressure. The residue is crystallized from ether to give the objective penicillin. Yield, 0.8 g. Purity (determined by iodometry), 88.3%.

EXAMPLE 6

Preparation of D-α-(4-ethoxycarbonyloxy-2,3-cyclohexenopyridine-5-carboxamido)-benzylpenicillin:

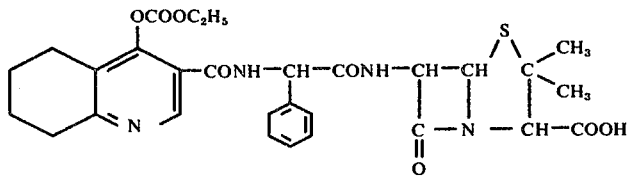

To 4-hydroxy-2,3-cyclohexenopyridine-5-carboxylic acid (0.9 g) are added dichloromethane (40 ml) and triethylamine (0.9 g), and ethyl chlorocarbonate (0.975 g) is added thereto at −20° to −15° C. After stirring for 20 minutes at the same temperature, α-aminobenzylpenicillin sodium salt (1.8 g) is added to the resulting mixture which is kept subsequently for 4 hours at the same temperature. The reaction mixture is treated as in Example 1 to give the objective penicillin (0.7 g). Purity (determined by iodometry), 94%.

EXAMPLE 7

Preparation of D-α-(2,4-dihydroxypyrimidine-5-carboxamido)-benzylpenicillin:

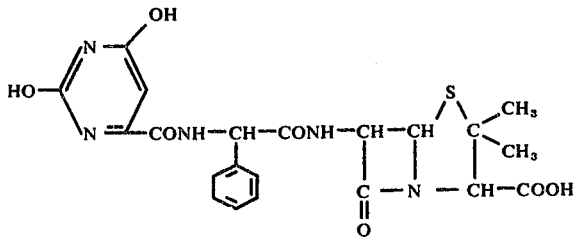

a. Uracil-5-carboxylic acid (1.0 g) is dissolved in dry pyridine (20 ml) under heating. p-Nitrophenyl trifluroacetate (1.8 g) is added to the solution which is subsequently stirred at 45° C for 30 minutes. Then, the solution is concentrated to dryness under reduced pressure, and the cyrstals thus obtained are washed with chloroform and then acetone to give the active ester, i.e. p-nitrophenyl 2,4-dihydroxypyrimidine-5-carboxylate (1.16 g). M.P. 298°–299° C (decomp.).

b. To a solution of α-aminobenzylpenicillin triethylamine salt (1.5 g) in dichloromethane (30 ml) are added the active ester (1.01 g) and dimethylformamide (50 ml) at room temperature. The resulting mixture is stirred at room temperature for 2.5 hours and concentrated under reduced pressure. Dichloromethane (40 ml) is added to the residue, and the solution is extracted three times with 60 ml portions of an aqueous solution of sodium bicarbonate. The extracts are combined together and admixed with ethyl acetate (50 ml). The mixture is adjusted to pH 2 with 1N hydrochloric acid. The ethyl acetate layer is separated, and the aqueous layer is extracted twice with ethyl acetate. The ethyl acetate layer and the ethyl acetate extract are combined together, washed with an aqueous solution of sodium chloride and dried over magnesium sulfate. To the dried ethyl acetate solution is added dropwise a mixture of a 50% solution of potassium 2-ethylhexanoate (1.2 g) in n-butanol with ether (30 ml). The white precipitate is collected by filtration, washed with ether and dried over phosphorus pentoxide under reduced pressure to give the objective penicillin as the potassium salt (0.7 g). Purity (determined by iodometry), 90%.

EXAMPLE 8

Preparation of D-α-(3-hydroxypyridazine-4-carboxamido)-benzylpenicillin:

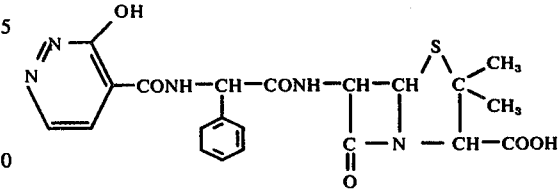

1. α-Aminobenzylpenicillin triethylamine salt (3.0 g) is dissolved in dichloromethane (50 ml), and p-nitrophenyl 3-hydroxypyridazine-4-carboxylate (M.P. 233° C, decomp.) (1.90 g) and dimethylformamide (30 ml) are added thereto in order while stirring at room temperature. Stirring is continued at room temperature for 17 hours. The separated crystals are collected by filtration, washed with ether and dried under reduced pressure to give the objective penicillin as the triethylamine salt (2.9 g). Purity (determined by iodometry), 93%.

2. α-Aminobenzylpenicillin 3,5-di-t-butyl-4-hydroxybenzyl ester (3.72 g), prepared from benzylpenicillin 3,5-di-t-butyl-4-hydroxybenzyl ester via 3,5-di-t-butyl- 4-hydroxybenzyl ester of 6-aminopenicillanic acid, is dissolved in dichloromethane (50 ml). To the resulting solution is added at room temperature p-nitrophenyl 3-hydroxypyridazine-4-carboxylate (1.90 g), and dimethylformamide (30 ml) is added thereto. The mixture is kept overnight at room temperature while stirring and evaporated under reduced pressure to remove dichloromethane. The residual solution is added to cold water (200 ml). The precipitate is collected by filtration, dried and added to a mixture of dimethylformamide (30 ml) and sodium thiophenolate (1.15 g). The resulting solution is poured into acetone (200 ml) and heated at 50° to 55° C while stirring. The precipitate is collected by filtration while hot, washed with acetone and dissolved in water (50 ml). The solution is adjusted to pH 2 with hydrochloric acid. The separated crystals are collected by filtration, washed with cold water and dried over phosphorus pentoxide under reduced pressure to give the objective penicillin. Purity (determined by iodometry), 89.5%.

EXAMPLE 9

Preparation of D-α-(4-hydroxypyridine-3-carboxamido)-p-hydroxybenzylpenicillin:

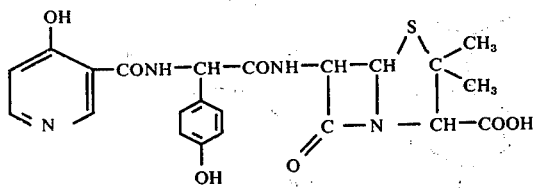

1. D-α-amino-p-hydroxybenzylpenicillin triethylamine salt (1.17 g) is dissolved in dimethylformamide (25 ml), and p-nitrophenyl 4-hydroxypyridine-3-carboxylate (M.P. 256°–258° C, decomp.) (0.65 g) and triethylamine (0.5 g) are added thereto in order while stirring at room temperature. Stirring is continued at room temperature for 4 hours. To the resulting solution is added acetone (125 ml), and the separated crystals are collected by filtration, washed with acetone and dissolved in water (50 ml). The solution is adjusted to pH 2 with hydrochloric acid while cooling. The separated crystals are collected by filtration, washed with cold water and dried over phosphorus pentoxide under reduced pressure to give the objective penicillin (0.77 g).

2. D-α-(4-hydroxypyridine-3-carboxamido)-p-hydroxybenzylpenicillin (0.77 g) is dissolved in a solution of dimethylformamide (8 ml) and acetone (35 ml). A solution of sodium 2-ethylhexanoate (0.256 g) in acetone (8 ml) is added thereto while stirring at room temperature. Stirring is continued at room temperature for 20 minutes. The separated crystals are collected by filtration, washed with acetone and dried under reduced pressure to give the objective penicillin as the sodium salt (0.75 g). Purity (determined by iodometry), 88%.

EXAMPLE 10

Preparation of D-α-(2-hydroxypyridine-3-carboxamido)-p-hydroxybenzylpenicillin:

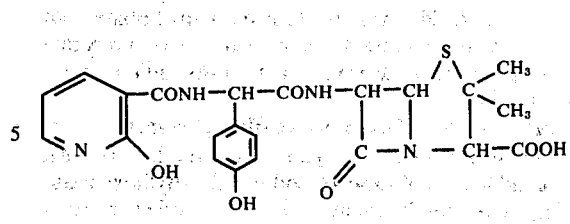

1. To D-α-amino-p-hydroxybenzylpenicillin trihydrate (0.84 g) are added dimethylformamide (20 ml), molecular sieve power 3A (1 g) and triethylamine (0.4 g). After stirring at room temperature for 20 minutes, the resulting mixture is filtered. To the filtrate, there is added p-nitrophenyl 2-hydroxypyridine-3-carboxylate (M.P. 234°–238° C) (0.52 g) while stirring at room temperature. Stirring is continued at room temperature for 3 hours. To the resulting solution, there is added ether (200 ml), and the precipitated crystals are collected by filtration, washed with ether and dissolved in water (50 ml). The solution is adjusted to pH 2 with hydrochloric acid while cooling. The precipitated crystals are collected by filtration, washed with cold water and dried over phosphorus pentoxide under reduced pressure to give the objective penicillin (0.69 g).

2. D-α-(2-Hydroxypyridine-3-carboxamido)-p-hydroxy-benzylpenicillin (0.69 g) is dissolved in a solution of dimethylformamide (7 ml) and acetone (15 ml). A solution of sodium 2-ethylhexanoate (0.266 g) in acetone (15 ml) is added thereto while stirring at room temperature. Stirring is continued at room temperature for 20 minutes. The precipitated crystals are collected by filtration, washed with acetone and dried under reduced pressure to give the objective penicillin as the sodium salt (0.705 g). Purity (determined by iodometry), 90%.

EXAMPLE 11

Preparation of D-α-(4-hydroxypyridine-3-carboxamido)-1,4-cyclohexadienylmethylpenicillin:

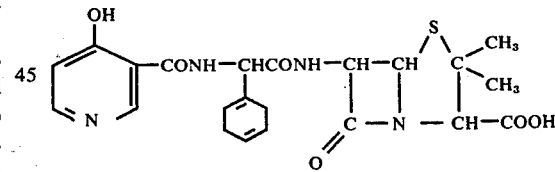

1. To 4-hydroxypyridine-3-carboxylic acid (3.0 g), there are added dichloromethane (150 ml) and triethylamine (4.60 g), and isobutyl chloroformate (6.50 g) is added thereto at −20° C. After stirring for 30 minutes, D-α-amino-1,4-cyclohexadienylmethylpenicillin triethylamine salt (9.7 g) is added to the resulting mixture, which is kept subsequently for 4 hours at −20° C. On completion of the reaction, a solution of sodium bicarbonate (4.3 g) in water (200 ml) and ethyl acetate (400 ml) is added thereto. The organic layer is separated from the aqueous layer and washed with water (25 ml). The aqueous layer and the washings are combined together, washed twice with ethylacetate and then cooled with ice. The aqueous solution is adjusted to pH 2 by the addition of dilute aqueous hydrochloric acid and extracted with ethyl acetate (200 ml). The extract is washed with water, dried over anhydrous magnesium sulfate and concentrated under reduced pressure. The residue is recrystallized from a mixture of ether and ethyl acetate to give D-α-(4-isobutoxycarbonyloxypyridine-3-carboxamido)-1,4-hexadienylmethylpenicillin (8 g).

2. (a) To D-α-(4-isobutoxycarbonyloxypryidine-3-carboxamido)-1,4-hexadienylmethylpenicillin (4 g), there is added a solution of sodium 2-ethylhexanoate (1.37 g) in dimethylformamide (20 ml) while stirring at room temperature. Stirring is continued for 20 minutes. To the resulting solution, there is added ether (100 ml), and the precipitated crystals are collected by filtration, washed with ether and dried under reduced pressure to give the objective penicillin as the sodium salt (2.9 g).

Purity (determined by iodometry), 91%.

(b) To D-α-(4-isobutoxycarbonyloxypyridine-3-carboxamido)-1,4-hexadienylmethylpenicillin (4 g), there is added a solution of potassium carbonate (1.5 g) in water (40 ml), and the resulting solution is stirred at room temperature for 1 hour and then adjusted to pH 2 with dilute hydrochloric acid while cooling with ice. Precipitated white crystals are collected by filtration, washed with water and dried under reduced pressure to give the objective penicillin. Yield, 3.1 g.

EXAMPLES 12 to 37

The new penicillins as shown in Table 1 are prepared in the same manner mentioned above.

Table 1

Q—CONH—CH(Z)—CONH—CH—CH—S—C(CH₃)₂—CH—COOM (penicillin core structure)

| Example No. | Compound Q | Z | M | Purity (%) (iodometry) |
|---|---|---|---|---|
| 12 | 3-OH-4-methyl-pyridazine | cyclohexenyl | Na | 90 |
| 13 | 3-OH-4-methyl-pyridazine | (CH₃)₂CH—CH₂— | Na | 82 |
| 14 | 3-OH-4-methyl-pyrimidine | (CH₃)₂CH—CH₂— | Na | 86 |
| 15 | 3-OH-4-methyl-pyridazine | thienyl (S) | Na | 89 |
| 16 | 3-OH-4-methyl-pyridine | thiazolyl (N,S) | Na | 89.5 |
| 17 | 3-OH-4-methyl-pyrimidine | thienyl (S) | Na | 83 |
| 18 | 3-OH-4-methyl-pyridazine | thienyl (S) | Na | 88 |
| 19 | 3-OH-4-methyl-pyridazine | thiazolyl (N,S) | Na | 88 |
| 20 | 4-OH-3-methyl-cycloheptapyridine | phenyl | H | 85 |

Table 1-continued

Structure:
Q—CONH—CH(Z)—CONH—CH—CH—C(CH₃)₂—S (β-lactam with N—CH—COOM)

| Example No. | Compound Q | Z | M | Purity (%) (iodometry) |
|---|---|---|---|---|
| 21 | 3-methyl-4-(OCOOC₂H₅)-5,6,7,8-tetrahydroquinolin-2-yl | phenyl | H | 92.5 |
| 22 | 2-methyl-3-(1-hydroxyethyl)-4-hydroxy-5-methylpyridin-... | phenyl | K | 92 |
| 23 | 2-azidomethyl-3-benzoyl-4-hydroxy-5-methylpyridin-... | phenyl | H | 89 |
| 24 | 3-hydroxy-4-methyl-6-methylpyridazin-... | phenyl | K | 92.5 |
| 25 | 4-hydroxy-5-methylpyridin-... | phenyl | K | 93 |
| 26 | 2-mercapto-4-hydroxy-5-methylpyrimidin-... | phenyl | H | 92 |
| 27 | 2-methylthio-4-hydroxy-5-methylpyrimidin-... | phenyl | H | 82 |
| 28 | 4-hydroxy-5-methylpyrimidin-... | phenyl | K | 91 |
| 29 | 6-chloro-3-hydroxy-4-methylpyridazin-... | phenyl | K | 87 |
| 30 | 3-(1-hydroxyethyl)-4-hydroxy-5-methylpyridin-... | phenyl | K | 89 |

Table 1-continued

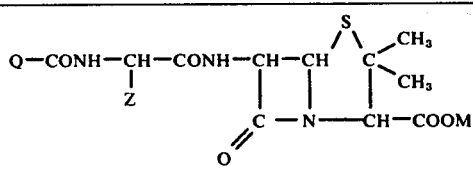

| Example No. | Compound Q | Z | M | Purity (%) (iodometry) |
|---|---|---|---|---|
| 31 | [cyclopenta-fused pyridine with =O and OH, CH3] | phenyl | K | 83 |
| 32 | [pyridine with NC, CH3, H3C, OH] | phenyl | K | 85 |
| 33 | [pyridine with OH, OH, CH3] | phenyl | K | 90.5 |
| 34 | [pyridine with CH3, OH] | phenyl | K | 93 |
| 35 | [pyrazine with OH, CH3] | phenyl | Na | 85 |
| 36 | [pyrimidine with O-COOC$_2$H$_5$, CH3, HS] | phenyl | H | 80 |
| 37 | [pyridazine with OH, CH3] | phenyl | K | 89 |

When determined according to the agar dilution method, the penicillins in the Examples afford the minimal inhibitory concentrations as shown in Table 2.

| | MIC (μg/ml) | | | | | |
|---|---|---|---|---|---|---|
| No. | Staphylococcus aureus 209P | Escherichia coli NIHJ | Proteus mirabilis GN2425 | Proteus vulgaris HX19 | Klebsiella pneumoniae 602 | Pseudomonas aeruginosa 104 |
| 1 | 0.39 | 12.5 | 3.13 | 0.05 | 6.25 | 6.25 |
| 2 | 0.39 | 25 | 12.5 | 0.39 | 12.5 | 12.5 |
| 3 | 0.78 | 12.5 | 6.25 | 0.39 | 6.25 | 12.5 |
| 4 | 0.78 | 12.5 | 6.25 | 0.39 | 12.5 | 12.5 |
| 5 | 0.78 | 12.5 | 6.25 | 0.39 | 6.25 | 12.5 |
| 6 | 0.78 | 12.5 | 6.25 | 0.39 | 6.25 | 12.5 |
| 7 | 0.39 | 12.5 | 6.25 | 0.05 | 25 | 3.13 |
| 8 | 0.39 | 12.5 | 6.25 | 0.05 | 6.25 | 3.13 |
| 9 | 0.78 | 12.5 | 6.25 | 0.2 | 100 | 3.13 |
| 10 | 1.56 | 12.5 | 12.5 | 0.2 | 100 | 6.25 |
| 11 | 0.39 | 25 | 12.5 | 0.2 | 12.5 | 6.25 |
| 12 | 0.2 | 12.5 | 12.5 | 0.05 | 3.13 | 3.13 |
| 13 | 0.39 | 12.5 | 25 | 0.39 | 25 | 12.5 |
| 14 | 0.78 | 25 | 25 | 0.39 | 50 | 12.5 |
| 15 | 0.39 | 12.5 | 6.25 | 0.05 | 12.5 | 3.13 |

-continued

| No. | Staphylococcus aureus 209P | Escherichia coli NIHJ | Proteus mirabilis GN2425 | Proteus vulgaris HX19 | Klebsiella pneumoniae 602 | Pseudomonas aeruginosa 104 |
|---|---|---|---|---|---|---|
| 16 | 0.78 | 25 | 12.5 | 0.2 | 25 | 6.25 |
| 17 | 0.39 | 25 | 6.25 | 0.05 | 50 | 3.13 |
| 18 | 0.39 | 12.5 | 6.25 | 0.05 | 12.5 | 3.13 |
| 19 | 0.39 | 12.5 | 6.25 | 0.05 | 25 | 6.25 |
| 20 | 0.78 | 25 | 6.25 | 0.78 | 3.13 | 12.5 |
| 21 | 0.78 | 25 | 6.25 | 0.78 | 3.13 | 25 |
| 22 | 0.78 | 25 | 12.5 | 0.39 | 12.5 | 6.25 |
| 23 | 1.56 | 12.5 | 6.25 | 0.2 | 3.13 | 25 |
| 24 | 0.39 | 12.5 | 50 | 0.39 | 25 | 3.13 |
| 25 | 0.78 | 50 | 12.5 | 0.2 | 25 | 6.23 |
| 26 | 0.78 | 25 | 3.13 | 0.05 | 50 | 3.13 |
| 27 | 0.78 | 50 | 12.5 | 0.1 | 50 | 6.25 |
| 28 | 0.39 | 25 | 12.5 | 0.05 | 100 | 3.13 |
| 29 | 0.2 | 12.5 | 50 | 0.39 | 25 | 12.5 |
| 30 | 0.78 | 6.25 | 12.5 | 0.2 | 25 | 12.5 |
| 31 | 0.78 | 6.25 | 3.13 | 0.057 | 50 | 12.5 |
| 32 | 0.78 | 12.5 | 50 | 0.78 | 100 | 12.5 |
| 33 | 0.2 | 6.25 | 25 | 0.2 | 25 | 6.25 |
| 34 | 0.39 | 12.5 | 25 | 0.2 | 25 | 6.25 |
| 35 | 0.78 | 25 | 25 | 0.78 | 25 | 3.13 |
| 36 | 0.78 | 25 | 3.13 | 0.05 | 25 | 6.25 |
| 37 | 0.39 | 12.5 | 12.5 | 0.2 | 12.5 | 3.13 |
| I | 0.78 | 100 | 50 | 0.39 | 50 | 50 |
| II | 0.78 | 100 | 100 | 0.78 | 100 | 50 |
| Ampicillin | 0.1 | 6.26 | 1.56 | 1.56 | 50 | >200 |

Remark: Compounds Nos. I and II are penicillins of the following formulas disclosed in U.S. Pat. No. 3,433,784:

No. I

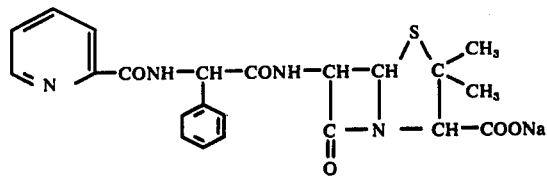

No. II

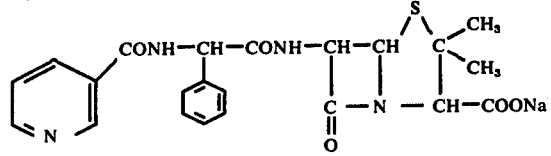

What is claimed is:

1. D-α-(4-Ethoxycarbonyloxy-2,3-cyclopentenopyridine-5-carboxamido)benzylpenicillin and non-toxic, pharmaceutically acceptable salts thereof.

2. D-α-(4-Hydroxy-2,3-cyclopentenopyridine-5-carboxamido)benzylpenicillin and non-toxic, pharmaceutically acceptable salts thereof.

3. D-α-(4-Hydroxy-2,3-cyclohexenopyridine-5-carboxamido)benzylpenicillin and non-toxic, pharmaceutically acceptable salts thereof.

4. D-α-(3-Acetyl-4-hydroxy-2-methylpyridine-5-carboxamido)benzylpenicillin and non-toxic, pharmaceutically acceptable salts thereof.

5. D-α-(2,3-Cyclohexeno-4-pivaloyloxypyridine-5-carboxamido)benzylpenicillin and non-toxic, pharmaceutically acceptable salts thereof.

6. D-α-(4-Ethoxycarbonyloxy-2,3-cyclohexeno-pyridine-5-carboxamido)benzylpenicillin and non-toxic, pharmaceutically acceptable salts thereof.

7. D-α-(2,4-Dihydroxypyrimidine-5-carboxamido)-benzylpenicillin and non-toxic, pharmaceutically acceptable salts thereof.

8. D-α-(3-Hydroxypyridine-4-carboxamido)benzylpenicillin and non-toxic, pharmaceutically acceptable salts thereof.

9. D-α-(4-Hydroxypyridine-3-carboxamido)benzylpenicillin and non-toxic, pharmaceutically acceptable salts thereof.

10. D-α-(4-Hydroxy-2,3-cycloheptenopyridine-5-carboxamido)benzylpenicillin and non-toxic, pharmaceutically acceptable salts thereof.

11. D-α-(4-Ethoxycarbonyloxy-2,3-cycloheptenopyridine-5-carboxamido)benzylpenicillin and non-toxic, pharmaceutically acceptable salts thereof.

12. D-α-[3-(α-Hydroxyethyl)-4-hydroxy-2-methylpyridine-5-carboxamido]benzylpenicillin and non-toxic, pharmaceutically acceptable salts thereof.

13. D-α-(3-Benzoyl-4-hydroxy-2-methylpyridine-5-carboxamido)benzylpenicillin and non-toxic, pharmaceutically acceptable salts thereof.

14. D-α-(3-Hydroxy-6-methylpyridazine-5-carboxamido)-benzylpenicillin and non-toxic, pharmaceutically acceptable salts thereof.

15. D-α-(2-Mercapto-4-hydroxypyrimidine-5-carboxamido)-benzylpenicillin and non-toxic, pharmaceutically acceptable salts thereof.

16. D-α-(4-Hydroxy-2-methylthiopyrimidine-5-carboxamido)-benzylpenicillin and non-toxic, pharmaceutically acceptable salts thereof.

17. D-α-(4-Hydroxypyrimidine-5-carboxamido)benzylpenicillin and non-toxic, pharmaceutically acceptable salts thereof.

18. D-α-(3-Hydroxypyridine-2-carboxamido)benzylpenicillin and non-toxic, pharmaceutically acceptable salts thereof.

19. D-α-(2-Hydroxypyrazine-3-carboxamido)benzylpenicillin and non-toxic, pharmaceuticaly acceptable salts thereof.

20. D-α-(4-Hydroxypyridazine-5-carboxamido)benzylpenicillin and non-toxic, pharmaceutically acceptable salts thereof.

* * * * *